United States Patent [19]

Balique

[11] Patent Number: 4,545,387
[45] Date of Patent: Oct. 8, 1985

[54] APPARATUS FOR RECORDING, CONTROL AND EARLY DETECTION OF CARDIOVASCULAR DISEASES

[76] Inventor: Georges A. Balique, Evasion 2000, 22 rue Emeriau, Paris, France

[21] Appl. No.: 444,379

[22] Filed: Nov. 26, 1982

Related U.S. Application Data

[63] Continuation-in-part of Ser. No. 170,574, Jul. 21, 1980, abandoned.

[30] Foreign Application Priority Data

Jul. 24, 1979 [FR] France .................... 79 19061

[51] Int. Cl.[4] .................................. A61B 5/02
[52] U.S. Cl. ............................ 128/687; 128/688; 128/663; 128/664; 128/666
[58] Field of Search .............. 128/633, 662–667, 128/670–672, 696, 694

[56] References Cited

U.S. PATENT DOCUMENTS

| | | | |
|---|---|---|---|
| 3,734,086 | 5/1973 | Phelps, Sr. .................. | 128/687 |
| 3,742,938 | 7/1973 | Stern ........................... | 128/687 |
| 3,773,033 | 11/1973 | Rodbard et al. .............. | 128/687 |
| 3,796,213 | 3/1974 | Stephens ...................... | 128/687 |
| 3,993,047 | 11/1976 | Peek ............................. | 128/687 |
| 3,996,928 | 12/1976 | Marx ............................ | 128/671 |
| 4,013,067 | 3/1977 | Kresse et al. ................. | 128/666 |
| 4,063,551 | 12/1977 | Sweeney ....................... | 128/666 |

FOREIGN PATENT DOCUMENTS

| | | | |
|---|---|---|---|
| 1466830 | 5/1964 | Fed. Rep. of Germany ...... | 128/666 |
| 2016648 | 8/1970 | France .......................... | 128/666 |
| 2239974 | 3/1975 | France .......................... | 128/664 |
| 2299003 | 8/1976 | France .......................... | 128/687 |

OTHER PUBLICATIONS

Geddes, L. A. et al., "Multifunction Transducer for Obtaining Digital Volume Pulse, Resistance and EKG," MBEC 1977, vol. 15, pp. 228–232.
Tursley, B. et al., "Automated Cuff-Pressure System" IEEE BME Trans., vol. 19, No. 4, 7-1972, pp. 271–276.

Primary Examiner—Kyle L. Howell
Assistant Examiner—Francis J. Jaworski
Attorney, Agent, or Firm—Steinberg & Raskin

[57] ABSTRACT

Apparatus for recording, control and early detection of cardiovascular diseases by detection, recording and/or audible and/or visual display of the heart beat frequency and rhythm from a digital pulse provided by a plethysmographic process at a given spot of the body, such as a finger of a hand, includes a digital pulse sensing device. The pulse sensing device consists of a determined frequency generator and an associated sensor, processing circuits, a recording device and/or audible and/or visual display devices. The apparatus includes at least two transducer devices of different physical natures, the output signal of which are processed separately and/or together to provide more accurate information about the heart beat frequency rhythm.

10 Claims, 7 Drawing Figures

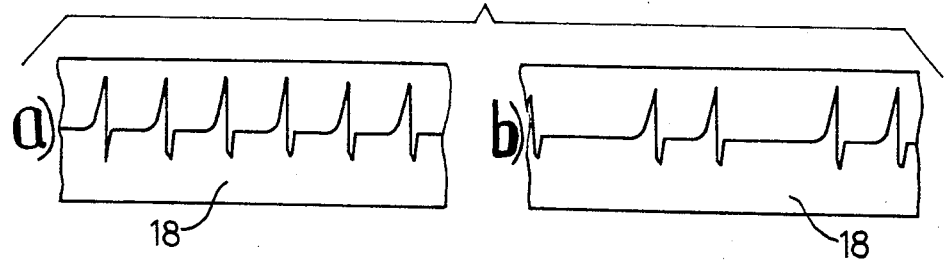
Fig: 5.
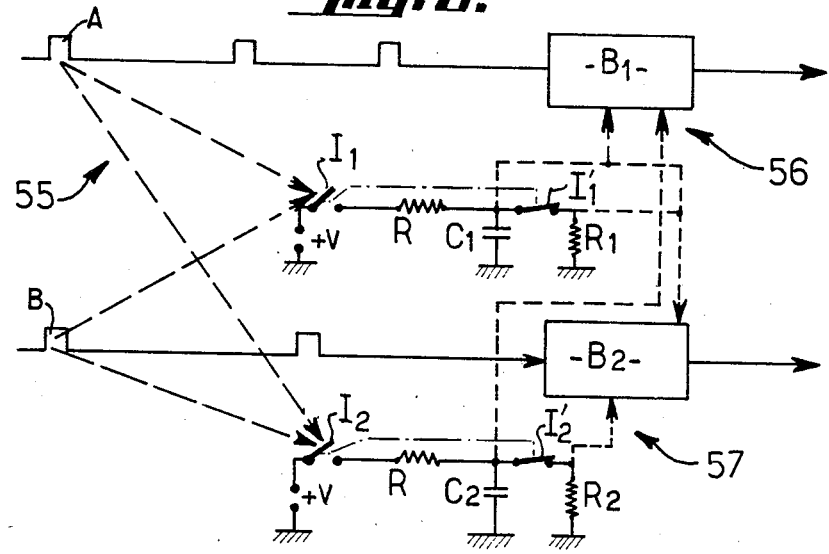
Fig: 6.
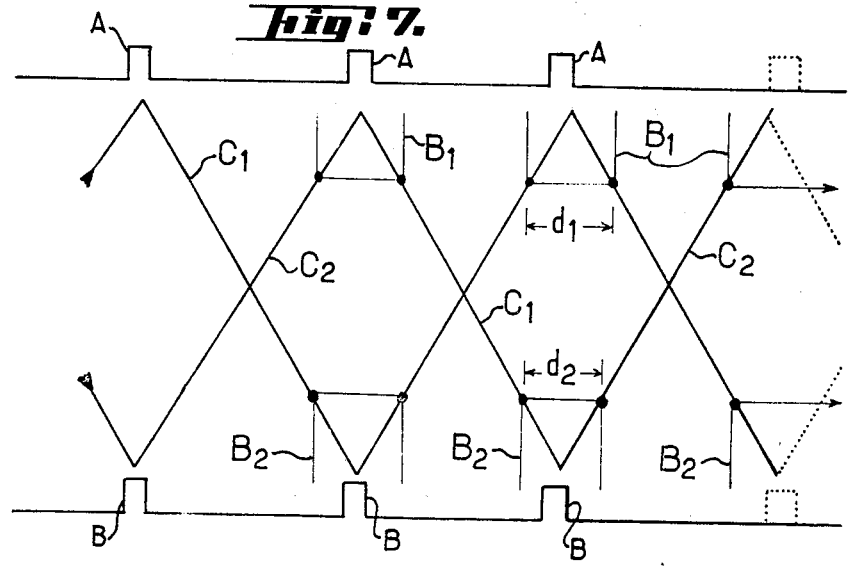
Fig: 7.

APPARATUS FOR RECORDING, CONTROL AND EARLY DETECTION OF CARDIOVASCULAR DISEASES

BACKGROUND OF THE INVENTION

This is a Continuation-in-Part of application Ser. No. 170,574, filed July 21, 1980, for Apparatus for Recording, Control and Early Detection of Cardiovascular Diseases, and now abandoned.

The present invention relates to apparatus for recording, control or testing and early detection or tracking down or checkup of cardiovascular diseases.

Many reports and statistical data regularly emphasize the continuously growing increase of cardiovascular diseases, which are one of the primary causes of mortality and increased death rate. Such diseases do not bypass those persons who often erroneously consider themselves as being in good health. The detection or tracking down of heart arrhythmia is essentially based on the electrocardiogram; such a test or examination should however in any case be carried out by a specialist in a doctor's consulting-room. In most cases, such testing or examination is performed during the presence of the disease. In other words, there is no early detection of the disease, whereas statistical data show that an initial early detection would be much beneficial.

It has therefore become indispensable for obvious reasons, to early detect or track down to the utmost such cardiovascular diseases otherwise than through the mere advice to proceed periodically with suitable tests, controls, checkup and like examinations. Such an approach may not a priori yield satisfactory results, because most people are reluctant and unwilling to make tests as long as they deem their state of health to be satisfactory.

SUMMARY OF THE INVENTION

The principal object of the invention is to provide apparatus for the early detection and prevention of cardiovascular diseases.

An object of the invention is to provide apparatus which is simple in use and is adapted to be made available to the general public at suitable places.

Another object of the invention is to provide apparatus able to forthwith show up, without the assistance of any specialist, any anomaly or disturbance of the heart beat rhythm.

Still another object of the invention is to provide apparatus which, although it does not supply an electrocardiogram, supplies simplified information which sufficiently discloses, in particular, heart beat rhythm characteristic periodical phenomena easily interpreted and handled or analyzed.

Yet another object of the invention is to provide apparatus for detecting heart beat frequency and rhythm, which apparatus is simple to use.

Another object of the invention is to provide apparatus for detecting heart beat frequency and rhythm, which apparatus functions as a health guide.

Still another object of the invention is to provide apparatus for detecting heart beat frequency and rhythm, which apparatus is automatic and does not require either a skilled operator or a specialist for interpreting the results.

The apparatus of the invention is accordingly adapted to record in particular the heart beat frequency and rhythm from the recording of the digital pulse picked up through any simple or complicated plethysmographic process. With such a process, it is possible to show up the change in volume of one or several organs under the influence of variations in the vessels which are irrigating or feeding this or these organs.

More specifically, during the ventricular contraction, the heart would eject a certain amount of blood which travels along the arterial vessels and gives rise at some location of the arterial system to a displacement of the walls of the artery. Such a displacement is sensed at at least one selected spot of the body, such as the end of a finger of a hand, for example. Thus is obtained a mechanical translation of the passing of a certain amount of blood to a given place of the body.

This manner of proceeding does not record the pulse, because this would require a special apparatus to obtain an analog curve of the displacement of the artery walls (sphygmogram), but involves the sensing of the pulse beats where physically elementary data is gathered or picked-up. Thus, with such an apparatus, the mechanical phenomenon of the displacement of the walls of an artery at a particular spot thereof is sensed and this phenomenon will be repeated x times every minute (frequency per minute) with a time period between each occurrence of the phenomenon which is either constant or not (regularity or irregularity). Stated otherwise, such an apparatus provides an artifacted plot or setting out consisting of a series of like pulses, each pulse corresponding to a beat of the pulse which is sensed by means of a suitable device.

The invention provides apparatus for recording, controlling or testing or checking and for early detection or tracking down of cardiovascular diseases through the sensing, recording and/or audible and/or visual display of the heart beat frequency and rhythm from the recording of the digital pulse picked-up through a plethysmographic process at a determined spot of the body such as a finger of the hand, for example. The apparatus comprises a digital pulse transducer device consisting of a generator for producing a determined frequency or emission and of an associated sensor, processing circuits, a recording and/or audible and/or visual display device. In accordance with the invention, the apparatus comprises at least two transducer devices of different physical natures, the output signals of which are processed separately and/or together in order to yield more accurate information about the heart beat frequency and rhythm.

Another feature of the invention is that the transducer devices used are optical, infrared ray, ultrasonic devices, or devices using high frequency oscillators having a very low level, ultrasonic devices using the so-called "Howling" effect, etc. These devices are located at the same place of the human body, or at different places, in particular, when the transducer devices are of the same physical nature, so as to avoid as much as possible interference phenomena.

Still another feature of the invention is the use of transducer devices which use a high frequency oscillator of a very low level comprising an oscillating circuit such as a transistor having an emitter coupling, with oscillation amplitude control to constantly take-up or compensate for the amplitude attenuation or weakening of the oscillations (power loss) resulting from the increase in the volume of the artery due to the oncoming rush or flow of blood.

Yet another feature of the invention is that the transducer devices, which use ultrasonic Howling effect oscillators, comprise an amplifying loop and a measuring loop to extract the pulses representative of the pulse beats.

A feature of the invention is the inclusion in the apparatus of at least one correlating circuit in order to predetermine the oncome of a pulse issuing from a transducer device in accordance with at least one of the foregoing already sensed pulses.

Another feature of the invention is the use of at least two different type transducer devices located around a finger of a hand of a person in proximity with each other. These transducer devices avoid, as much as possible, interference phenomena. In fact, the use of two identical transducers such as infrared detection devices permits interference phenomena to occur with output signals from the corresponding sensors. This problem is resolved by the apparatus of the invention.

In accordance with the invention, apparatus for recording, controlling and early detecting of cardiovascular diseases by detection, recording and visual and audible display of the heart beat frequency and rhythm from a digital pulse recording picked up by a plethysmographic process at a finger of a hand of a person, comprises at least two transducer devices of different types, each in operative proximity around the finger. Each of the transducer devices has a generator for providing a signal of a determined frequency and an associated sensor for sensing signals from the generator. The sensor provides an output signal modulated in amplitude by expansion of the blood vessel walls in the finger. A multiplexing unit is connected to the transducer devices and processes output signals from the sensors of the transducer devices to select signals from the transducer devices which are representative of information about heart beat frequency and rhythm. A display device connected to the multiplexing unit visibly and audibly displays the information and records the information.

One of the transducer devices comprises a high frequency infrared generator and another of the transducer devices comprises a high frequency oscillator having emitter coupling, a very low level and an amplitude feedback loop.

One of the transducer devices comprises a high frequency infrared generator and another of the transducer devices comprises a high frequency ultrasonic generator.

The transducer devices are positioned at two different places of the finger.

One of the transducer devices comprises a high frequency oscillator having emitter coupling, a very low level and an amplitude feedback loop.

At least one correlating circuit predetermines the oncome of a pulse from one of the transducer devices in accordance with at least one of the pulses already detected by another of the transducer devices.

The high frequency oscillator comprises an oscillating transistor having an emitter, a base, a collector, an emitter circuit and a collector circuit. A first tuned circuit is connected in the collector circuit. A second tuned circuit is connected in the emitter circuit. A pickup circuit is connected to the collector for deriving a small part of the high frequency signal from the transistor to provide a picked-up signal. An amplifier is connected to the pickup circuit for amplifying the picked-up signal to provide an amplified signal. A differentiating network is connected to the amplifier for decoupling the amplified signal to provide a differentiated signal. A detecting circuit is connected to the differentiating network for detecting the differentiated signal to provide a detected signal. A control circuit is connected to the detecting circuit and coupled to the base of the oscillating transistor. The control circuit drives the transistor with the detected signal.

The correlating circuit comprises at least two capacitors, charge and discharge devices for substantially constant charging and discharging of the capacitors and at least two threshold flip-flops associated with the capacitors.

The control circuit consists of two transistors connected in a Darlington circuit.

The flip-flops are associated with the transducer devices and selectively pass and block pulses emitted from the transducer devices during a time predetermined by the capacitors.

BRIEF DESCRIPTION OF THE DRAWINGS

For a fuller understanding of the invention, reference is had to the following description, taken in connection with the accompanying drawings, in which:

FIG. 5 is a graphic presentation of test results obtained by the apparatus of the invention;

FIG. 6 is a block and circuit diagram showing an embodiment of a correlating circuit of the apparatus of the invention with iterative predetermination for determining in advance the oncome of a test pulse; and FIG. 7 is a graphic presentation of the principle of operation of the circuit of FIG. 6.

DESCRIPTION OF PREFERRED EMBODIMENTS

Figure 1:
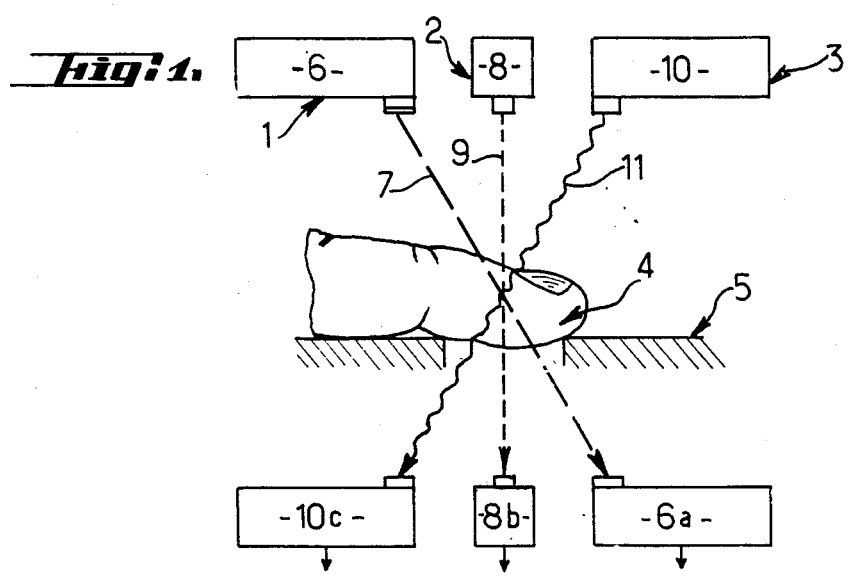
FIG. 1 is a block diagram of a system utilizing several devices for detecting the digital pulse at one finger of a user of the apparatus of the invention.

FIG. 1 diagrammatically shows three transducer devices 1, 2, 3 of the apparatus of the invention. Each transducer device is adapted to sense the digital pulse at, for example, a finger 4 of the hand of a user of said apparatus. The finger 4 is placed on a support or rest 5.

The transducer device 1 is, for example, a conventional optical transducer device comprising a light source or generator 6 emitting light or a light beam 7 received by an associated light sensor 6a.

The transducer device 2 is, for example, a conventional ultrasonic transducer device of acoustic type, or possibly of electromagnetic type comprising an ultrasonic generator 8 emitting ultrasonic frequencies 9 received by an associated ultrasonic sensor 8b. The frequency of the ultrasonic beam is, for example, several megaHertz.

The transducer device 3 is, for example, an infrared ray transducer device comprising an infrared source or generator 10 providing an infrared beam 11 received by an associated infrared sensor 10c. The infrared rays may have a wavelength of 900 nanometers, for example.

All of these transducer devices are shown as operating in the transmission mode. That is, a generator and its associated sensor are located on opposite sides of the finger 4. It is, however, possible to operate according to the deep reflection mode. That is, a generator and its associated sensor are positioned on the same side of the finger 4. This is preferable, for example, in a device for optical detection in visible light.

Figure 2:
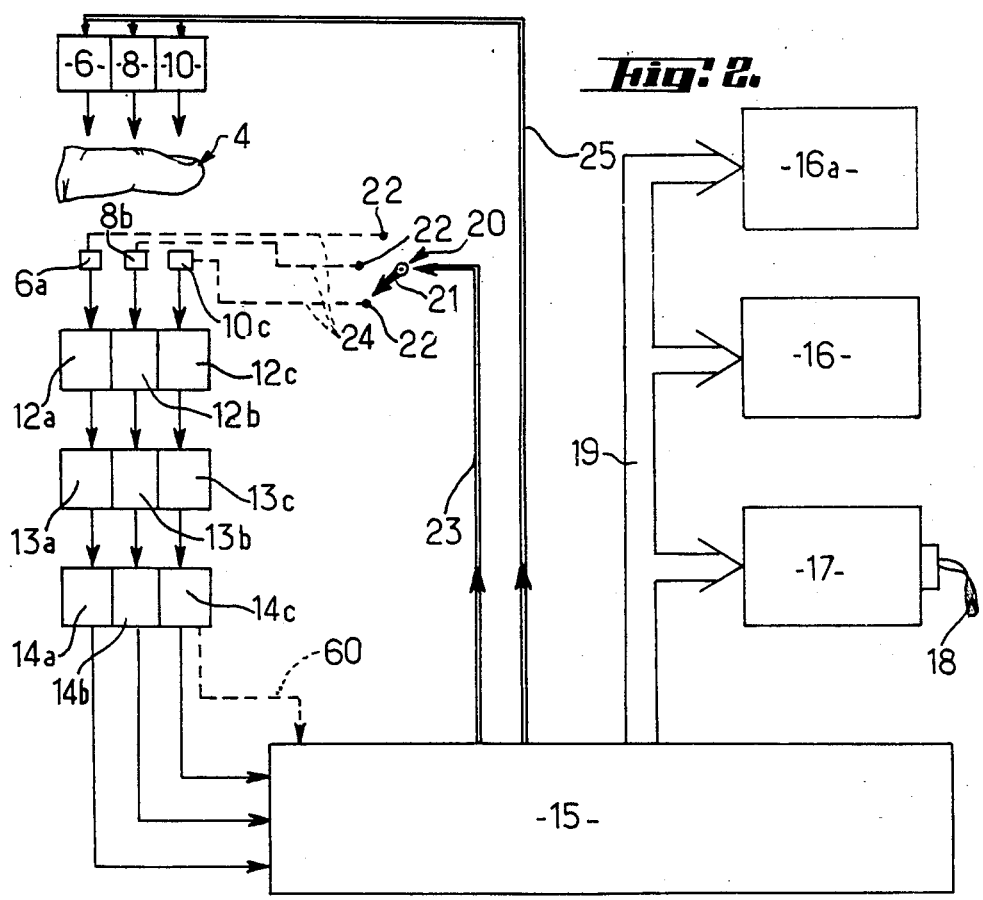
FIG. 2 is a block diagram of an embodiment of the main processing circuits of the apparatus of the invention.

In FIG. 2, the outputs of the sensors 6a, 8b and 10c are connected to the inputs of three detectors 12a, 12b and 12c, respectively. The outputs of the three detectors 12a, 12b and 12c are connected to three amplifiers 13a, 13b and 13c, respectively. The outputs of the amplifiers, after shaping by circuits 14a, 14b and 14c, are connected to the inputs of a multiplexing unit 15 performing several functions. The functions performed by the multiplexing unit 15 permit the following.

The visual presentation of the heart beat frequency and rhythm of the user on a display device 16 or the translation of the heart beat frequency and rhythm by an audible device 16a.

The recording of the heart beat frequency and rhythm in a recorder 17 with printout, and, in particular, on a filigreed paper strip or tape 18 created to comply with the needs. The visual display device 16, the audible device 16a and the recorder 17 are connected to outputs of the multiplexing unit 15 via a data bus 19.

The possible selection of a particular sensor 6a, 8b or 10c in accordance with the data gathered or collected by the multiplexing unit 15 from these sensors. For this purpose, the apparatus comprises, for example, a selector or switch 20, having a movable armature or yoke 21 automatically controlled or actuated by a data bus 23 leading from the multiplexing unit 15. The switch 20 also has stationary contacts 22 which cooperate with the movable armature or yoke 21 in order to select one or the other of the sensors. The contacts 22 are connected through lead lines 24 to the sensors 6a, 8b and 10c.

Figure 3:
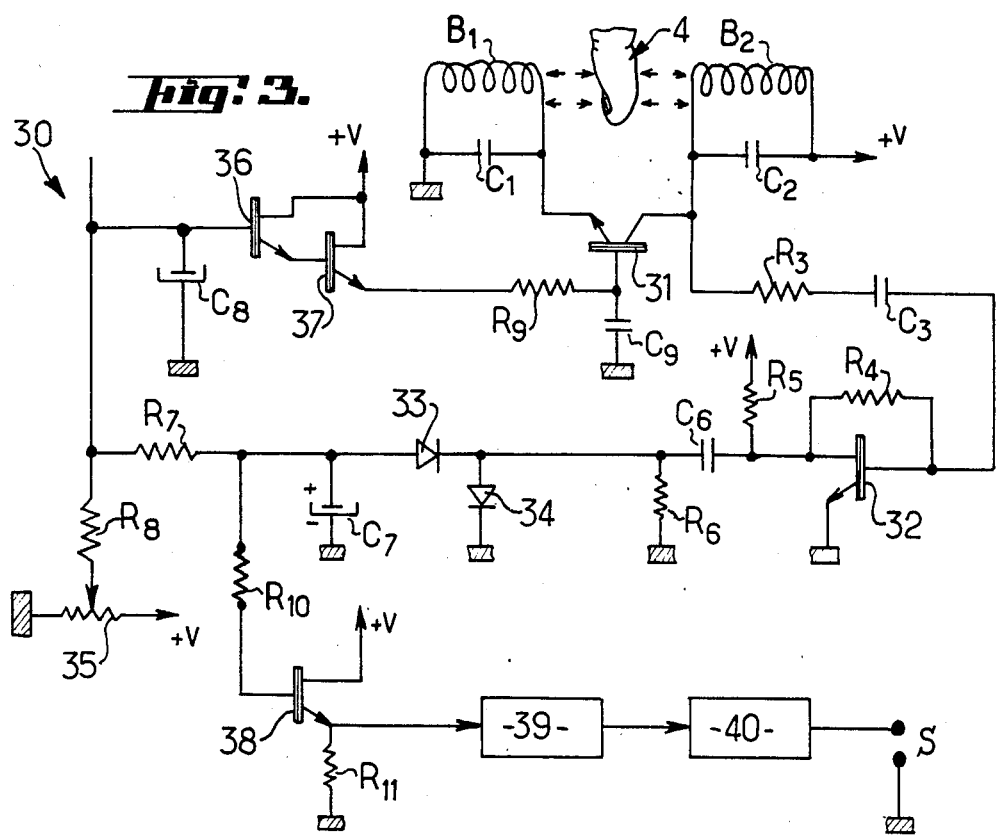
FIG. 3 is a circuit diagram of an embodiment of the first transducer device of the apparatus of the invention.

FIG. 3 shows a particular transducer device 30 which is a high frequency oscillator having a very low level and servo-controlled as an amplitude loop.

The transducer device 30 comprises an oscillating transistor 31 with emitter coupling. The emitter of the transistor 31 is connected to a tuned emitter circuit comprising a coil or winding $B_1$, one end of which is connected to said emitter of said transistor and the other end of which is connected to ground. A capacitor $C_1$ is possibly connected in parallel with, or across, the winding $B_1$ to improve the oscillation.

The collector of the oscillating transistor 31 is connected to a tuned collector circuit comprising a coil or winding $B_2$, one end of which is connected to the collector of said transistor and the other end of which is connected to a voltage supply (+V). A capacitor $C_2$ is connected in parallel with, or across, the winding $B_2$.

The collector of the oscillating transistor 31 is preferably connected to a RC network for taking the high frequency signal from the oscillator. The RC network comprises a resistor $R_3$ and a capacitor $C_3$ connected in series.

The terminal of the capacitor $C_3$ farthest from the resistor $R_3$ is connected to the base of an amplifying transistor 32, the emitter of which is grounded. A resistor $R_4$ is connected between the collector and base of the transistor 32 to provide the bias and the negative or reverse feedback of said transistor. The collector of the amplifying transistor 32 is connected to the voltage source (+V) via a load resistor $R_5$.

The collector of the amplifying transistor 32 is connected to a differentiating decoupling circuit comprising a capacitor $C_6$ and a grounded resistor $R_6$. The differentiating circuit $R_6$, $C_6$ is connected to a detecting circuit consisting of two diodes 33 and 34. The connecting point between the resistor $R_6$ and the capacitor $C_6$ is connected to the cathode of the diode 33. The anode of the diode 34 is connected to the cathode of the diode 33 and its cathode is grounded. The anode of the diode 33 is connected to a detection filter capacitor $C_7$.

The point of connection between the diode 33 and the capacitor $C_7$ is connected to two current-limiting resistors $R_7$ and $R_8$ connected in series. The other end of the resistor $R_8$ is connected to a sliding contact of a potentiometer 35 for adjusting the amplitude of the oscillations of the transistor 31 through the Darlington circuit, hereinafter described.

The point of connection between the current-limiting resistors $R_7$ and $R_8$ is connected to a drive circuit for controlling the base current of the oscillating transistor 31 via an interposed filter capacitor $C_8$. The control or drive circuit consists of two transistors 36 and 37 arranged as a "Darlington" circuit. The emitter of the transistor 37 is connected to one end of a resistor $R_9$ for limiting the base current of the oscillating transistor 31. The other end of the resistor $R_9$ is connected to the base of the transistor 31 and is also connected to ground via a high frequency decoupling capacitor $C_9$.

The output of the transducer device 30 is at the point of connection between the detecting capacitor $C_7$ and the current-limiting resistor $R_7$. This point of connection is connected to the base of a current amplifying transistor 38 via a resistor $R_{10}$. The collector of the transistor 38 is connected to a voltage supply source (+V) and the emitter of said transistor is connected to ground via a load resistor $R_{11}$. The amplified signal is derived from the emitter of the impedance-matching amplifying transistor 38 to drive a bandpass filter 39 and then a shaping circuit 40 to obtain usable primary or elementary information.

Figure 4:
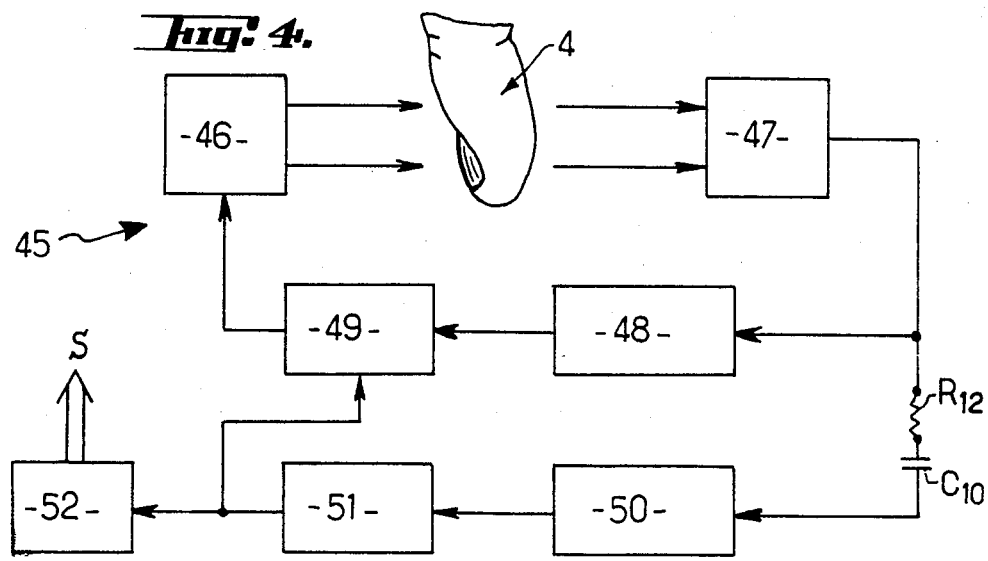
FIG. 4 is a block diagram of an embodiment of the second transducer device of the apparatus of the invention.

FIG. 4 shows another type of transducer device of the invention. The transducer device 45 of FIG. 4 is an ultrasonic device comprising an ultrasonic generating circuit 46 and an ultrasonic receiver circuit 47 for receiving the emitted ultrasonic frequencies, an oscillation loop and a coupling loop. The oscillation loop comprises an amplifier 48, the input of which is connected to the output of the receiver 47. The output of the amplifier 48 is connected to the input of an attenuator 49, the output of which is connected to the ultrasonic generator 46.

The coupling loop comprises an oscillation-taking circuit consisting of a resistor $R_{12}$ and a capacitor $C_{10}$ connected in series, or any other type of coupling system. The resistor $R_{12}$ is connected to the output of the ultrasonic receiver 47 and the capacitor $C_{10}$ is connected to a measuring amplifier 50. The output of the amplifier 50 is connected to a detection stage 51 which provides AC to DC conversion of the signals it receives. The DC, or continuous, signals at the output of the detecting stage 51 make it possible to control or drive the attenuator 49, which is a DC-controlled unit, for example. The servo-control loop take-up or hunting signals at the output of the detector 51 are also processed and shaped by a shaper circuit 52 in order to obtain a signal usable by the multiplexing unit 15, at the output S.

The apparatus also comprises at least one correlating circuit 55, shown in FIG. 6. The correlating circuit permits the predetermination of the oncome of a pulse output by a transducer device in accordance with at least one of the foregoing pulses already sensed at another transducer device. The correlating circuit 55 comprises a first circuit 56 essentially comprising a circuit (voltage v, resistor R) for charging a capacitor $C_1$ with a constant current via an interposed switch $I_1$, and a circuit for discharging the capacitor $C_1$ with a constant current resistor $R_1$ via an interposed switch $I'_1$ mechanically coupled to the switch $I_1$, for example. The discharge circuit is connected to the control or drive inputs of two threshold flip-flops, or multivibrator, or toggle circuits $B_1$ and $B_2$. The correlating circuit 55 further comprises a second circuit 57 like the foregoing one and consisting of a circuit for charging (voltage v, resistor R) a capacitor $C_2$ with a constant current via an interposed switch $I_2$, and a circuit for discharging the capacitor $C_2$ with a constant current, consisting of a resistor $R_2$ via an interposed switch $I'_2$, mechanically coupled to the switch $I_2$, for example. This discharge circuit is connected to the control or drive inputs of the two threshold flip-flop, or multivibrator, or toggle circuits $B_1$ and $B_2$.

The connections of the correlating circuit 55 is hereinafter described in greater detail in the explanation of the operation of the apparatus.

The aforedescribed apparatus operates as follows.

The user who desires to effect a test begins at first to put the apparatus into operation by any suitable means such as, for example, presence of the finger, push-button, insertion of a coin into a slot of the apparatus. If the apparatus includes conventional transducer devices 1, 2 and 3 (FIGS. 1 and 2), the gate voltage or switching on of the apparatus causes energizing of the generators 6, 8 and 10. In the absence of a foreign substance or body intercepting the frequencies or emissions 7, 9 and 11 of the generators 6, 8 and 10, respectively, the sensors 6a, 8b and 10c, respectively, associated with said generators receive the whole emissions. The detectors 12a, 12b and 12c, associated with the sensors 6a, 8b and 10c, respectively, which are sensitive or responsive to amplitude variations of the electric signals supplied by the sensors 6a, 8b and 10c, respectively, deliver no output signal, since there is no disturbance of the emissions 7, 9 and 11 of the generators 6, 8 and 10, respectively. The multiplexing unit 15 receives no signal and only an indicating or monitor lamp is energized in the visual display device 16, meaning that the apparatus is switched on, that is, it is alive or has voltage applied to it.

After switching on, the user properly positions one finger of his hand at a place or spot clearly shown on the apparatus to disturb the different emissions of all the generators of the transducer devices 1, 2 and 3.

The emission 7 of the light source or generator 6 is partly absorbed by the finger 4 of the user, so that the light sensor 6a associated with said light source delivers a signal of smaller amplitude. This amplitude variation is detected by the detector 12a, which in turn generates a signal amplified by the associated amplifier 13a and shaped by the associated shaping circuit 14a. This signal is then received by the multiplexing unit 15.

The emissions 9 and 11 of the ultrasonic generator 8 and the infrared source 10, respectively, are also disturbed and the signals emitted by the ultrasonic sensor 8b and the infrared sensor 10c processed like the signal emitted by the light sensor 6a.

In the exemplary embodiment shown, the multiplexing unit 15 accordingly receives three signals which in fact are not interesting for the test, because they only show the presence of a foreign body or substance in the paths of the emissions of the transducer devices 1, 2 and 3. If this foreign body is inert, the multiplexing unit 15 no longer receives any signal. If, on the contrary, the foreign body has a varying volume, the energy absorbed by such body varies and this is reflected in amplitude and/or frequency variations of the signals at the outputs of the sensors 6a, 8b and 10c. In the contemplated application, this change in volume occurs at the vessel which expands at each oncoming flow or rush of blood. In other words, there are amplitude variations in the signals emitted by the sensors 6a, 8b and 10c. These amplitude variations therefore result in signals which are received by the multiplexing unit 15.

The function of the multiplexing unit is to compare, mix, correlate, interpolate, etc. these different signals received in order to analyze or interpret them with a view to extract exhaustive information or data with high reliability and very high probability of veracity or truthfulness on the one hand, as well as secondary information or data which is indirect or indirectly inferred on the other hand. This information or data, and in particular, the digital pulse frequency, is then sent through the medium of the data bus 19 to the visual display device 16 and/or to the audible device 16a, and/or to the recording device 17 with printing on a filigreed paper strip or tape 18.

FIG. 5 shows two artifacted plots a and b, respectively, which represent two heart beat frequencies, respectively, recorded on the filigreed strip or tape 18. The artifacted plot a shows a normal heart beat frequency and the artifacted plot b shows an abnormal heart beat frequency. The analysis or handling of these artifacted plots is obvious for the user, who will be able to draw the necessary conclusions therefrom.

It is possible to control the switch 20 to select, for example, a particular sensor which is likely to give the best results. As a matter of fact, since the transducer devices are of different physical natures, they may respond or react differently against the user.

The operation of the transducer device 30 of FIG. 3, which may advantageously be substituted for one of the transducer devices 1, 2 and 3 of FIG. 1 is hereinafter described.

Once the transducer device 30 is switched on, or has a voltage applied thereto, the oscillating transistor 31 generates oscillations at a very low level, of about a hundred millivolts. If a foreign body or member, is inserted between the two coils or windings $B_1$ and $B_2$ of the emitter circuit and the tuned collector circuit, respectively, there is a decrease in the amplitude of the oscillations due to the variation in the coefficient of voltage surge or overvoltage of the tuned circuit, as well as a change in the coupling between the emitter and the collector of the oscillating transistor 31. As previously, the oncoming rushes or flows of blood in the vessels of the finger 4 interposed between the windings $B_1$ and $B_2$ change the amplitudes of the oscillations from the transistor 31 each time.

A very small portion of the oscillations present at the collector of the transistor 31 is transmitted via the resistor $R_3$ and the capacitor $C_3$. It is necessary to transmit only a very weak signal in order to avoid too large a weakening or attenuation which would make the oscillations collapse. For this reason, the coupling is very weak and in the case described the resistance $R_3$ is relatively high.

The signal transmitted by the pickup circuit $R_3$, $C_3$ is then amplified by the amplifying transistor 32. The amplified signal is decoupled by the differentiating circuit consisting of the capacitor $C_6$ and the resistor $R_6$. The positive pulses are then excluded via the diode 34 in order to retain only the negative pulses, which would pass through the diode 33. The negative signal is then subtracted from the initial signal of adjustment of the oscillating transistor 31 provided by the resistor $R_8$ and the potentiometer 35. The voltage at the point of connection of the resistors $R_7$ and $R_8$, that is the voltage at the base of the transistor 36 decreases and the voltage at the base of the oscillating transistor 31 is accordingly decreased. Under such circumstances, the collector-base voltage of the transistor 31 increases, whereby it is possible to compensate for the decrease of the oscillations caused by the oncoming flow of blood in the finger 4. There is accordingly provided a very high oscillator with a very low level which is servo-controlled in follow-up or feedback relationship in an amplitude loop. The negative pulses at the output of the diode 33 resulting from an electronic hunting or taking-up of the feedback or servo-control loop are taken and amplified by the amplifier transistor 38 and processed by the processing circuits 39 and 40 in order to obtain at the output S pulses workable by the multiplexing unit 15.

FIG. 4 shows another embodiment of a transducer device 45 of the invention. The transducer device 45 is an ultrasonic device using the Howling effect. The ultrasonic frequencies emitted by the ultrasonic generator 46 are received by the ultrasonic detector or receiver 47. The oscillation pulses at the output of the receiver 47 are amplified by the amplifier 48 and then fed again to the generator 46 via a drivable or controllable attenuator 49. Under such circumstances, one portion of the output energy is fed again into the input to maintain the oscillations. As previously, the interposition of the finger 4 of the user between the ultrasonic generator 46 and the receiver 47, together with the oncoming flows or rushes of blood in said finger, induces amplitude variations of the oscillations at said receiver. A very small portion of the signal output by the receiver 47 is taken via the resistor $R_{12}$ and the capacitor $C_{10}$. This weak signal is amplified by the amplifier 50.

As in the transducer device described with reference to FIG. 3, only a weak signal should be taken or picked up, in order not to disturb the oscillations. The alternating signal picked up is then converted by the detector 51 into a continuous or DC signal, which makes it possible to drive or control the attenuator 49 in order to compensate for decreases in oscillation induced by the oncoming flows or rushes of blood in the finger 4 of the user. The signal at the output of the detector 51 is processed by the shaping circuits 52 in a conventional manner in order to provide pulses workable by the multiplexing unit 15 at the output S.

The operation of the correlating circuit 55 in order to predetermine the oncome of a pulse output by a transducer device in accordance with at least one of the pulses previously sensed by another transducer device is described with reference to FIGS. 6 and 7.

It is assumed that a pulse A is present at the input of the correlating circuit 55. The pulse A opens the switch $I_2$ of the circuit 57 and closes the switch $I'_2$ to permit the "previously charged" capacitor $C_2$ to discharge with a constant current into the resistor $R_2$. When the voltage at the terminals of the capacitor $C_2$ is the threshold voltage of the flip flop $B_2$, said flip-flop is made conducting. From such time, the flip-flop $B_2$ passes the pulses from a second transducer device received at its input. Normally, a few moments later, a pulse B output by the second transducer device occurs and causes a switchover of the switch $I_2$ of the circuit 57 to enable the capacitor $C_2$ to be charged again with a constant current. The capacitor $C_2$ is no longer able to discharge into the resistor $R_2$ because the switch $I'_2$ is open in synchronism with the switch $I_2$. When the charge of the capacitor $C_2$ again reaches the tripping or triggering threshold of the flip-flop $B_2$, said flip-flop becomes non-conducting. This determines a duration $d_1$ during which the flip-flop $B_2$ is on or conducting.

With the capacitor C charging, said capacitor will reach the tripping or triggering threshold of the flip-flop $B_1$ and cause said flip-flop to become conducting in anticipation of the occurrence of a pulse A. At the oncome of the pulse A from the first transducer, the switch $I_2$ is again switched over to provide for the discharge of the capacitor $C_2$ with a constant current. While discharging, the voltage of the capacitor $C_2$ again goes through the triggering threshold of the flip-flop $B_1$ to cause said flip-flop to become non-conducting again. This determines a duration $d_2$ during which the flip-flop $B_1$ becomes conducting in order to pass the information or data coming from the first transducer device.

If the anticipations are correct, the flip-flops $B_1$ and $B_2$ are made conducting just before the occurrence of a pulse and are then made non-conducting. On the contrary, when the pulse B fails to arrive once the flip-flop B has been made conducting, said flip-flop remains conducting and passes all the information or data coming from the second transducer device. In other words, the final information is not very selective. This reasoning, considering as the starting point the oncome of a pulse A, is exactly the same when considering the oncome of a pulse B, with a view to determine the occurrence of the next pulse A. In such a case, it is the circuit 56 which is to be considered. In fact, both circuits 56 and 57 operate simultaneously.

It is possible, when there is no occurrence of a pulse A or B, to compensate for this absence by feeding in a pulse which permits bringing the capacitor $C_1$ or $C_2$ back to normal operating limits. The circuit 55 therefore permits good selectivity of information in particular when the heart beat rhythm is relatively regular. The correlating circuit 55 may be connected in the input of the multiplexing unit 15. That is, the pulses which pass through the flip-flops $B_1$ and $B_2$ are transmitted to the multiplexing unit 15 with a view to provide for the visual and/or audible display and/or recording of the heart beat rhythm.

The correlating circuit 55 permits detection of the oncome of a pulse relating to cardiac information issued from a sensor. A few moments later, another pulse is output by a second detection device and relates to the same cardiac information. This is possible, because of angular and longitudinal shifting of the different detecting devices disposed around one finger of the patient. The correlating circuit assures that the pulses A and B are actually representative of the same cardiac information, which will be further processed in the multiplexing unit 15. Of course, it is necessary to adjust to an optimal value the time constant of charge and discharge of the capacitor $C_2$ or $C_1$ by acting on the resistor $R_2$ or $R_1$, so that the duration of the flip-flop conduction $B_2$ or $B_1$ be short enough to only conduct the pulse B or A and not to conduct anything else. The correlating circuit 55 provides for the establishment of a good selectivity of signal information, without recording any noise, in a normal range of cardiac frequency and rhythm. The correlating circuit may be connected in the multiplexing unit 15, instead of between the outputs of the transducers and said multiplexing unit, as shown in FIG. 2.

The multiplexing unit 15 may include filter means such as a bandpass filter, passing modulated signals from sensors and having a fixed frequency. The filter means blocks noise signals of frequencies different from those in the frequency range of said filter means. The correlating function of the multiplexing unit 15 may be performed by the correlating circuit 55 of FIG. 6. The correlating circuit 55 may also provide an interpolating or interpreting function in order to produce a pulse bringing the capacitor $C_1$ or $C_2$ back to normal operating limits during non-occurrence of the pulse A or B. By mixing signals from the filter means, it is always possible to pass at least one signal representative of cardiac information when other signals are representative of false information. In other words, the multiplexing unit 15 passes the three signals output by the three sensors and may itself select information truly representative of the cardiac frequency.

In the exemplary embodiment described, it has been considered that the three transducer devices are associated with one single finger 4 of the user. It is, of course, possible to provide the transducer devices on several fingers of the hand. The transducer device shown in FIG. 3 may, of course, be constructed of integrated circuits.

It should also be pointed out that the multiplexing unit 15 may receive analog information or data for possible servo-controlling or feedback purposes from the processing circuits treating the signals coming from the sensors. This possibility is shown in FIG. 2 by a connection 60 in broken lines.

The aforedescribed apparatus may also include other circuits in particular associated with the multiplexing unit 15 in order to permit indications, in the visual display device 16, for example, relating to the veracity or truthfulness of the information or data which is recorded or printed, for example, on the tape 18.

The recordings provided by the apparatus of the invention are of elementary, but accurate, character. That is, they permit the control, checking or testing of the heart beat rhythm and frequency. An abnormal rhythm may readily be early detected after having possibly carried out a second test to confirm the first one.

It is also possible, by using several transducer devices, to measure the blood flow propagation within the arteries. With a first transducer device, such as a palpitation or feeling sensor positioned on the heart, the heart beat is detected, and with a second transducer device, such as those hereinbefore described, the moment at which the oncome of the rush or flow of blood, at one finger of the user, for example, is detected. From these two measures it is easy to know the speed of propagation.

The expansion of the blood vessel walls of the finger 4 does not affect the frequency of the transducers. As a matter of fact, when the infrared radiation source is utilized, an oscillator energizes said radiation source to generate radiation pulses in the infrared region at a fixed frequency and the sensor senses infrared radiation pulses. When the finger is interposed between the infrared source and sensor, the pulsating blood flow changes the transmission of radiation pulses in the infrared region as a function of the amount of blood in that region, and thus modulates the amplitude of the infrared pulse signals. Furthermore, the modulated amplitude signals output by the transducer devices have the frequency of the heart rate and an amplitude variation proportional to the amplitude variation of the first pulse. These signals are processed by a suitable logical circuit in the multiplexing unit 15, so that they are displayed, recorded, and so on.

A feature of the invention is the use of at least two different type transducer devices located around a finger of a hand of a person in proximity with each other. These transducer devices avoid, as much as possible, interference phenomena. As a matter of fact, the use of two identical transducers such as an infrared detection device, permits interference phenomena to occur with output signals from the corresponding sensors. This problem is resolved by the apparatus of the invention.

The apparatus of the invention may therefore be made easily available to the general public and assists considerably in the control, testing, or check up, and the early detection or tracking down of, cardiovascular diseases.

The term "artifacted plot" explains an artificial graphic transportation of the natural phenomenon of cardiac frequency. As seen in FIG. 5, two artifacted plots a and b represent the graphic transportation of the cardiac frequency. Plot a shows a series of pulses representing a heart beat frequency which is normal and plot b shows an abnormal heart beat frequency due to a cardiac deficiency.

The "Larsen effect" corresponds to the "Howling effect" and is a phenomenon which occurs in a transmission canal when part of output energy is fed back to the input and induces spontaneous oscillations. The "Howling effect" is well known, for example, in amplification apparatus. In the present invention, the ultrasonic device 45 operates with the "Howling effect" for detecting heart beat frequencies.

The term "iterative predetermination" does not refer to an "iteration" used in association with computerized devices. In the present disclosure, "iterative" is intended to be synonymous with "frequentative", which means that the correlating circuit cyclically predetermines the oncome of a pulse issuing from a transducer device in accordance with at least one of the pulses previously sensed by another transducer device. Thus, detection of the oncome of a pulse in accordance with another pulse, previously sensed, is repeated due to the charge and discharge of the capacitors $C_1$ and $C_2$, which cause the flip-flops $B_1$ and $B_2$ to be conducting or non-conducting. All the transducer devices or sensors are not in simultaneous operation at a common point on the finger, as shown in FIG. 1. FIG. 1 merely shows three transducer devices operating in a transmission mode, but in no case do signals output by associated generators converge at the same point in the finger. Actually, the three transducers 6-6a, 8-8b and 10-10c are not in the same plane, as appears to be shown in FIG. 1, but are angularly shifted relative to each other around the finger. Consequently, the transmission mode of each transducer device is affected at different points in the finger by a change in volume occurring at the vessels which expand at each rush of blood.

Since the three transducer devices are also positioned at different places along the finger, the A-B determination circuitry can detect the oncome of one pulse from one sensor in accordance with another pulse previously sensed by another sensor. Two transducer devices or sensors can rapidly detect the arterial pulse waveform, so that the determination circuitry detects the oncome of the pulse in accordance with another, previously detected, pulse.

A logical circuit of the multiplexing unit 15 enables said multiplexing unit to compare, mix, correlate and interpolate. Thus, the multiplexing unit 15 is not only a single multiplexer, used as a switching device, but is intended to be a more electronic complex assembly which performs several functions. Thus, for example, the multiplexing unit includes comparison means such as, for example, a comparison filter for comparing the information issuing from the sensor with fixed values in order to eliminate some of this information, which does not correspond to the required values. The multiplexing unit 15 thus accomplishes a comparison function. Mixing, correlating, and interpolating functions may also be performed by known and appropriate circuits obvious to anyone skilled in the art, so that the filtered information is exhaustive, with high reliability and a very high probability of veracity.

The generator frequencies of servo-controlled sensors may be adjusted, if desired, from the multiplexing unit 15 by appropriate circuits. Thus, for example, the transducer device 30, shown in FIG. 3, including an oscillating circuit with an amplitude feedback loop, may have its frequency changed by acting on the frequency of a resonant circuit constituted by the capacitor $C_1$ and the winding $B_1$.

It should be understood that the invention is not at all limited to the embodiments described and shown, which have been given by way of illustration as examples only. In particular, it comprises all the means constituting technical equivalents of the means described, as well as their combinations, if same are carried out according to its gist and used within the scope of the appended claims.

The invention is by no means restricted to the aforementioned details, which are described only as examples; they may vary within the framework of the invention, as defined in the following claims.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. Apparatus for recording, controlling and early detecting of cardiovascular diseases by detection, recording, and visual and audible display of the heart beat frequency and rhythm from a digital pulse recording picked up by a plethysmographic process at a finger of a hand of a person, said apparatus comprising at least two different transducer devices of different types, each in operative proximity around said finger and each having a generator for providing a signal of a determined frequency and an associated sensor for sensing signals from said generator, said sensor providing an output signal modulated in amplitude by expansion of the blood vessel walls in said finger;

a multiplexing unit connected to said transducer devices and processing output signals from said sensors of said transducer devices to select signals from said transducer devices which are representative of information about the heart beat frequency and rhythm;

at least one correlating circuit connected between the output of said transducer devices and said multiplexing unit for predetermining the oncome of a pulse from one of said transducer devices in accordance with at least one of the pulses already detected by another of said transducer devices; and display means connected to said multiplexing unit for visually and audibly displaying said information and recording said information so that said information is always representative of the regularity of the heart beat frequency and rhythm when the latter is regular or of the irregularity of the heart beat frequency and rhythm when the latter is irregular.

2. Apparatus as claimed in claim 1, wherein one of said transducer devices comprises a high frequency infrared generator and another of said transducer devices comprises a high frequency oscillator having emitter coupling, a very low level and an amplitude feedback loop.

3. Apparatus as claimed in claim 1, wherein one of said transducer devices comprises a high frequency infrared generator and another of said transducer devices comprises a high frequency ultrasonic generator.

4. Apparatus as claimed in claim 1, wherein one of said transducer devices comprises a high frequency oscillator having emitter coupling, a very low level and an amplitude feedback loop.

5. Apparatus as claimed in claim 4, wherein said high frequency oscillator comprises an oscillating transistor having an emitter, a base, a collector, an emitter circuit and a collector circuit, a first tuned circuit connected in said collector circuit, a second tuned circuit connected in said emitter circuit, a pick-up circuit connected to said collector for deriving a small part of the high frequency signal from said transistor to provide a picked-up signal, an amplifier connected to said picked-up circuit for amplifying said picked-up signal to provide an amplified signal, a differentiating network connected to said amplifier for decoupling said amplified signal to provide a differentiated signal, a detecting circuit connected to said differentiating network for detecting the differentiated signal to provide a detected signal, and a control circuit connected to said detecting circuit and coupled to the base of said oscillating transistor.

6. Apparatus as claimed in claim 5, wherein said control circuit consists of two transistors connected in a Darlington circuit.

7. Apparatus as claimed in claim 1, wherein said correlating circuit comprises at least two capacitors, charge and discharge means for substantially constant charging and discharging of said capacitors and at least two threshold flip-flops associated with said capacitors.

8. Apparatus as claimed in claim 7, wherein said flip-flops are associated with said transducer devices and selectively pass and block pulses emitted from said transducer devices during a time predetermined by said capacitors.

9. Apparatus for recording, controlling, and early detecting of cardiovascular diseases by detection, recording, and visual and audible display of the heart beat frequency and rhythm from a digital pulse recording picked-up by a plethysmographic process at a finger of a hand of a person, said apparatus comprising
- at least two different transducer devices of different types, each in operative proximity around said finger and each having a generator for providing a signal of a determined frequency and an associated sensor for sensing signals from said generator, said sensor providing an output signal modulated in amplitude by expansion of the blood vessel walls in said finger;
- a multiplexing unit connected to said transducer devices and processing output signals from said sensors of said transducer devices to select signals from said transducer devices which are representative of information about the heart beat frequency and rhythm;
- at least one correlating circuit connected between the output of said transducers and said multiplexing unit for predetermining the oncome of a pulse from one of said transducer devices in accordance with at least one of the pulses already detected by another of said transducer devices, said correlating circuit comprising at least two capacitors, charge and discharge means for substantially constant charging and discharging of said capacitors and at least two threshold flip-flops associated with said capacitors, said flip-flops being associated with said transducer devices and selectively pass and block pulses emitted from said transducer devices during a time predetermined by said capacitors; and
- display means connected to said multiplexing unit for visually and audibly displaying said information and recording said information so that said information is always representative of the regularity of the heart beat frequency and rhythm when the latter is regular or of the irregularity of the heart beat frequency and rhythm when the latter is irregular.

10. Apparatus for recording, controlling and early detecting of cardiovascular diseases by detection, recording, and visual and audible display of the heart beat frequency and rhythm from a digital pulse picked-up by a plethysmographic process at a finger of a hand of a person, said apparatus comprising
- at least two different transducer devices of different types, each in operative proximity around said finger and each having a generator for providing a signal of a determined frequency and an associated sensor for sensing signals from said generator, said sensor providing an output signal modulated in amplitude by expansion of the blood vessel walls in said finger, one of said transducer devices comprising a high frequency oscillator having emitter coupling, a very low level and an amplitude feedback loop, said high frequency oscillator comprising an oscillating transistor having an emitter, a base, a collector, an emitter circuit and a collector circuit, a first tuned circuit connected in said collector circuit, a second tuned circuit connected in said emitter circuit, a pick-up circuit connected to said collector for deriving a small part of the high frequency signal from said transistor to provide a picked-up signal, an amplifier connected to said picked-up circuit for amplifying said picked-up signal to provide an amplified signal, a differentiating network connected to said amplifier for decoupling said amplified signal to provide a differentiated signal, a detecting circuit connected to said differentiating network for detecting the differentiated signal to provide a detected signal, and a control circuit connected to said detecting circuit and coupled to the base of said oscillating transistor, said control circuit driving said transistor with said detected signal;
- a multiplexing unit connected to said transducer devices and processing output signals from said sensors of said transducer devices to select signals from said transducer devices which are representative of information about the heart beat frequency and rhythm; and
- display means connected to said multiplexing unit for visually and audibly displaying said information and recording said information so that said information is always representative of the regularity of the heart beat frequency and rhythm when the latter is regular or of the irregularity of said beat frequency and rhythm when the latter is irregular.

* * * * *